United States Patent [19]

Byrum

[11] Plant 4,015

[45] Feb. 8, 1977

[54] YELLOW ROSE PLANT

[75] Inventor: Roy L. Byrum, Richmond, Ind.

[73] Assignee: Joseph H. Hill Company, Richmond, Ind.

[21] Appl. No.: 662,886

[22] Filed: Mar. 1, 1976

[51] Int. Cl.[2] ..... A01H 5/00
[52] U.S. Cl. ..... Plt./15
[58] Field of Search ..... Plt./15

*Primary Examiner*—Robert E. Bagwill
*Attorney, Agent, or Firm*—Chas. W. Rummler

[57] ABSTRACT

A new variety of hybrid tea rose intended for greenhouse culture and the commercial production of cut flowers, characterized by its abundant and continuous production of medium large, long pointed buds which when first cut, open up very well in the base to produce attractive, well formed, 4 to 5 inch flowers which have a distinctively strong tea fragrance and better than average vase life. This new rose plant has a vigorous, much branched growth habit and abundant foliage of large leaves which accentuate the brilliance of its yellow flowers.

1 Drawing Figure

YELLOW ROSE PLANT

BACKGROUND OF THE NEW PLANT

My new variety of rose plant is the result of breeding efforts carried on by me at Richmond, Ind., with the object of producing a yellow rose with improved growth and flower production as a commercial forcing plant for cut flowers. This plant is a seedling derived by my crossing of an unnamed Seedling No. 63-70Y with the variety "Golden Fantasie" (U.S. Plant Pat. No. 3,272) in the spring of 1969. The first flowers of this new plant appeared in the fall of 1970 and the attractive, darker yellow coloring and strong fragrance of the flowers led to propagation of the new plant for observation and test. The vigorous growth of the new plant and its continuous and abundant production of attractive blooms has resulted in its propagation on a commercial scale.

The seed parent of my new plant, Seedling No. 63-70Y, is the result of the cross of an imported variety of unknown origin, identified in my records as No. 59-E, with the variety "Anniversary" (U.S. Plant Pat. No. 2,084) as the pollen parent. This cross with "Anniversary" was made by me at Richmond, Ind., and subsequently the seedlings so produced were found to lack any degree of consistency in propagation. One of these seedlings (63-70Y), however, when crossed with "Golden Fantasie" (P.P. 3,272), resulted in the herein disclosed new variety of yellow rose which propagates very successfully and produces a much more vigorous bush with more production than either of its parents. The pollen of "Anniversary" is in the lineage of both parents of my new variety and the new plant exhibits all of its advantageous features.

Propagation of my new variety of rose plant is now being carried on by budding, under my direction, at Richmond, Ind., and at Hamilton City, Calif., and many generations of the new plant have shown that its distinctive and advantageous characteristics hold true from generation to generation and are firmly fixed.

DESCRIPTION OF THE DRAWING

This new variety of rose plant is illustrated by the accompanying photographic drawing which shows, in full color, the newly opened and three days opened flowers, several stages of bud opening from the time when the calyx breaks, top and under side views of typical leaves, and specimens of young and old wood, the colors shown being as nearly true as can be obtained by careful, conventional photographic procedures.

DESCRIPTION OF THE NEW PLANT

The following is a description, in detail, of my new rose plant variety with color designations according to Koster's Color Guide (K) and the Horticultural Colour Chart (HCC) issued by the British Colour Council in collaboration with The Royal Horticultural Society of London, England, the following data being from observations of greenhouse plants grown at Richmond, Ind.

THE PLANT

Origin: Seedling.
Parentage:
- *Seed parent.*—Unnamed Seedling No. 63-70Y.
- *Pollen parent.*—Golden Fantasie (P.P. 3,272).

Classification: Hybrid Tea.
Form: Bush.
Habit: Upright and much branched.
Growth: Free and vigorous.
Canes: Size—Of medium diameter.
Main Stems: Straight and strong.
- *Color.*—Sage Green, Plate 78 (K).
- *Thorns.*—Several, straight and of medium length with a long, narrow base. Color: Tobacco Brown, Plate 88 (K).
- *Prickles* and *Hairs.*—None.

Branches: Color Spinach Green 0960/1 (HCC).
- *Thorns.*—Several, straight and long with a long narrow base. Color: Erythrite Red 0027 (HCC) at the base gradually changing to 0027/1 toward the tip. Some thorns change to a transparent color at the very tip.
- *Prickles* and *Hairs.*—None.

New Shoots: Color—Nearest color is Deep Carmine Violet, Plate 46 (K).
- *Thorns.*—Several, slightly hooked downward with a long, narrow base. Color: Deep Carmine Violet, Plate 46 (K).
- *Prickles* and *Hairs.*—None.

Foliage: Quantity—Abundant.
- *Leaves.*—Size—Large. Shape—Odd pinnate.
- *Leaflets.*—3, 5 and 7 in number. Shape: Ovoid, with round base, acute apex and simply serrate margins. Color—Mature leaf: Upper surface—Nearest color is Spinach Green 0960 (HCC). Under surface—Nearest color is Sage Green, Plate 78(K). Young leaf: Upper surface—Nearest color is Deep Carmine Violet, Plate 46 (K). Under surface—Nearest color is Deep Carmine Violet, Plate 46 (K). Aspect—Heavy and leathery.

*Rachis.*—Medium heavy, with smooth, grooved upper side and sparsely prickly on the under side.

*Stipules.*—Medium in length, with very short points turning out at an angle of more than 45° from the stem.

THE BUD

Before the calyx breaks:

*Size.*—Medium large.

*Form.*—Long pointed, with a conspicuous neck and foliaceous appendages on the bud surface with parts extending beyond the bud tip a distance equal to one-half or more of the bud length.

*Color of Calyx.*—Scheeles Green 860/2 (HCC).

As the calyx breaks:

*Color, Outside of Petal.*—Chrome Yellow 605/1 (HCC). Some petals have a streak of Pod Green 061/2 (HCC) through the center.

As first petal opens:

*Bud Size.*—Medium large.

*Bud Form.*—Long pointed.

*Color.*—Outside—Chrome Yellow 605 (HCC) gradually changing to 605/1 (HCC) with some nearly white at the tip. Inside—Indian Yellow 6/1 (HCC) at the base gradually changing to 6/2 (HCC) at top. Some nearly white at the tip.

Bud Opening: Bud opens up very well in greenhouse.

Sepals:Permanent and of medium length, some straight and some spear-shaped.

*Color.*—Inside—Scheeles Green 860/3 (HCC) overlaid with white fuzz. Outside—Scheeles Green 860/2 (HCC) some having a light streak of Deep Carmine Violet, Plate 46 (K), toward end of sepal.

Peduncle: Erect and strong; of medium length and diameter.

*Bark.*—Smooth. Color—Spinach Green 0960/2 (HCC).

*Thorns, Prickles* and *Hairs.*—None.

THE FLOWER

Blooming Habit: Continuous and abundant.

Borne: Singly, on strong stems of medium length.

Size: Medium large, 4 to 5 inches in diameter when fully opened.

Form: Full and high centered at first, with petals remaining tightly rolled outward. Becoming open with the petals loosely rolled outward at maturity.

Petalage: Double—25 to 30 petals arranged regularly.

*Shape of Petals.*—Outside and intermediate petals are obovate with mucronate apex and having one notch. Inside petals are obovate with a retuse apex.

*Texture.*—Moderately thick.

*Aspect.*—Satiny on inside and outside.

Color of Petals: A. The following observations were made of a newly opened greenhouse grown flower in Jan. 1975.

Outside Petals

*Outside surface.*—Chrome Yellow 605 (HCC) gradually changing to 605/1 (HCC) toward the top.

*Inside surface.*—Lemon Yellow 4/1 (HCC) gradually changing to 4/2 (HCC) toward the top.

Intermediate and Inside Petals

*Outside surface.*—Same as outside petals.

*Inside surface.*—Same as outside petals.

Color of petals: B. The following observations were made of a flower that was opened for three days in a greenhouse in Jan. 1975.

All Petals

*Outside surface.*—Mimosa Yellow 602/1 (HCC) at the base changing through 602/2 to 602/3 (HCC) at the tip.

*Inside surface.*—Mimosa Yellow 602 (HCC) at the base gradually changing through 602/1 to 602/2 to 602/3 (HCC) at the tip.

General color effect of the open bloom:

*Newly opened flower.*—Mimosa Yellow 602 (HCC).

*Three days opened flower.*—Mimosa Yellow 602/2 (HCC).

Persistence: Petals hang on and dry.

Fragrance: Strong tea.

Lasting Quality: 4 to 5 days for the fully opened flower kept at living room temperature, Jan. 1975.

REPRODUCTIVE ORGANS

Stamens: Many in number arranged regularly about the pistils.

*Filaments.*—Long, most with anthers. Color—Some are Carmine Rose 621 (HCC) and some are Chrome Yellow 605 (HCC).

*Anthers.*—Medium large in size, All open at same time. Color—Chrome Yellow 605/2 (HCC).

*Pollen.*—Abundant. Color—Orange Buff 507/2 (HCC).

Pistils: Many.

*Styles.*—Short and uneven, moderately thin and bunched. Color—Crimson Carmine, Plate 41 (K).

*Stigmas.*—Creamy White, Plate 2 (K).

Ovularies: Some protruding from calyx.

Hips and Seeds: None.

This new rose plant variety most nearly resembles its pollen parent "Golden Fantasie" (U.S. Plant Pat. No. 3,272) in its pleasing fragrance, color, and flower. Its predominant difference, however, resides in its more vigorous growth producing more flowering canes which makes it more productive throughout the year as a greenhouse forcing variety. Also, it is practically disease resistant, especially to mildew.

The attractive pointed buds borne on sturdy, upright stems and the development of the flowers as they open in the vase, together with the lush green foliage which accentuates the brilliance of the strong yellow coloring of the flowers and the pronounced rose fragrance of the blooms, enhances and distinguishes this variety from most rose varities that are not so endowed.

I claim:

1. A new and distinct rose plant variety substantially as herein shown and described, characterized by the distinctive yellow color and the strong tea fragrance of its flowers, its vigorous growth, and its year around abundant production of blooms on strong upright stems.

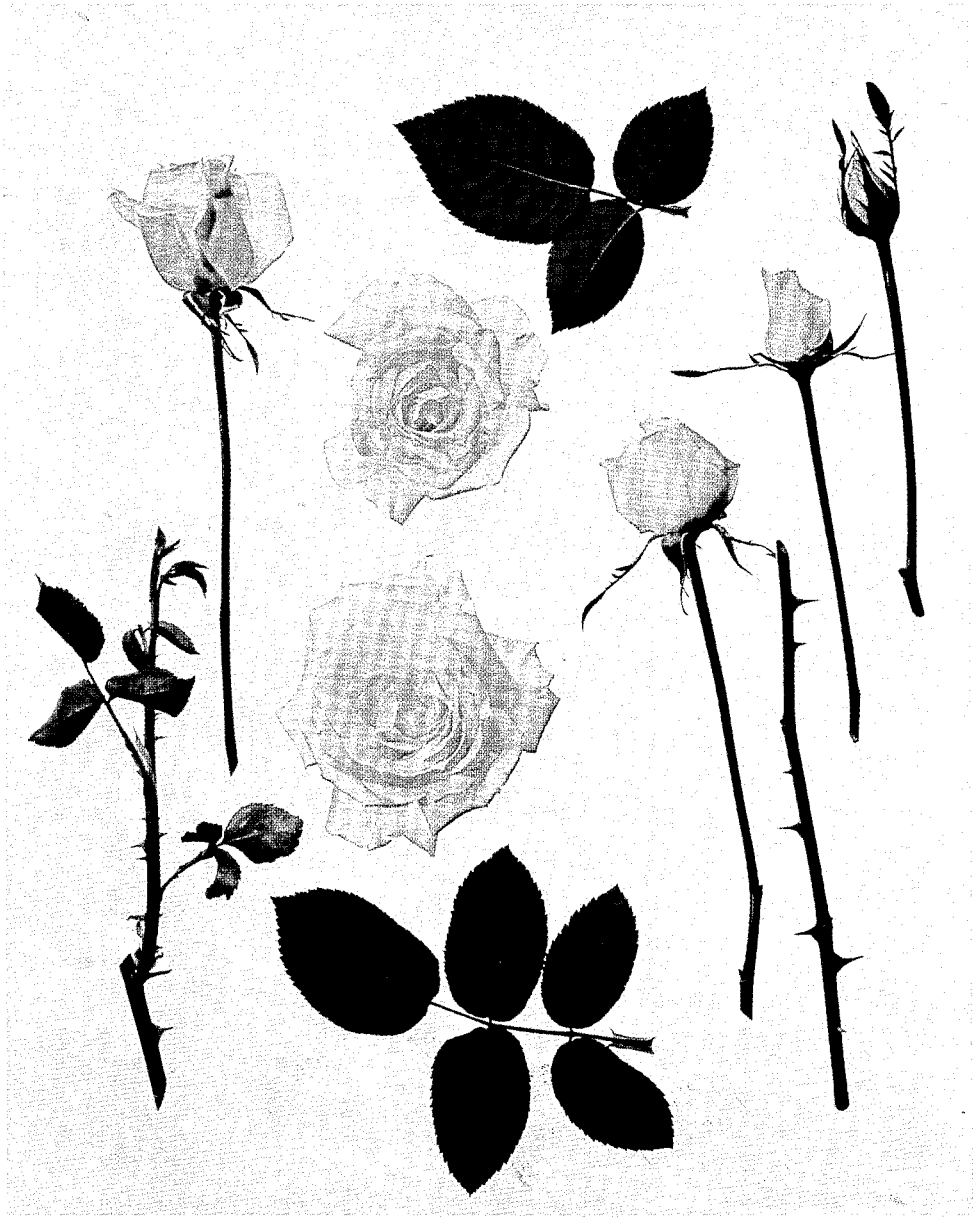

* * * * *